United States Patent [19]

Koumura et al.

[11] Patent Number: 4,591,554

[45] Date of Patent: May 27, 1986

[54] RAPID METHOD FOR DETECTING MICROORGANISMS

[75] Inventors: Ichiro Koumura, Sagamihara; Hideo Kanou, Yokosuka; Masahiko Okunishi, Tokyo; Kazuhiko Yamada, Fujisawa, all of Japan

[73] Assignee: Ajinomoto Co., Inc., Tokyo, Japan

[21] Appl. No.: 521,460

[22] Filed: Sep. 16, 1983

Related U.S. Application Data

[63] Continuation of Ser. No. 250,737, Apr. 3, 1981, abandoned.

[30] Foreign Application Priority Data

Oct. 31, 1979 [JP] Japan .................. 54-140582

[51] Int. Cl.⁴ .................. C12Q 1/34; C12Q 1/04; C12Q 1/06; C12Q 1/10
[52] U.S. Cl. .................. 435/18; 435/34; 435/38; 435/39
[58] Field of Search .................. 435/29, 34, 39, 38, 435/14, 18

[56] References Cited

U.S. PATENT DOCUMENTS

| | | | |
|---|---|---|---|
| 3,870,601 | 3/1975 | Warren et al. | 435/34 |
| 4,070,247 | 1/1978 | Burt | 435/38 |
| 4,242,447 | 12/1980 | Findl et al. | 435/808 |
| 4,259,442 | 3/1981 | Gayral | 435/14 |
| 4,308,348 | 12/1981 | Monget | 435/38 |

OTHER PUBLICATIONS

Ishikawa et al., Scandinavian J. Immunology, Quantitative Enzyme Immunoassays, Suppl. 7, vol. 8, Blackwell Scientific Pub., London, 43-55 (1978).

*Primary Examiner*—Esther M. Kepplinger
*Attorney, Agent, or Firm*—Oblon, Fisher, Spivak, McClelland & Maier

[57] ABSTRACT

A small number of microorganisms can be rapidly detected or determined by means of a fluorescence analysis method using specific umbelliferone derivatives such as 4-methylumbelliferyl phosphate and 4-methyl umbelliferyl galactoside, and this detecting method is applicable for a microbial inspection on sanitary quality of various kind of food, beverage, water and toilet article, or for a clinical inspection on a microbial infection.

11 Claims, 1 Drawing Figure

RAPID METHOD FOR DETECTING MICROORGANISMS

This is a continuation of U.S. application Ser. No. 250,737 entitled "A Rapid Method for Detecting Microorganisms" by the same inventors filed on Apr. 3, 1981, abandoned.

BACKGROUND OF THE INVENTION

1. Field of the Invention

The present invention relates to a rapid method for detecting microorganisms by means of a fluorescence analysis method using umbelliferone derivative.

2. Description of prior art

It has been socially demanded to keep food and beverage free from microbial contamination, and it is provided by Japanese law that the food such as edible meat, soft drink and fish paste product should not contain any coliform organisms.

Therefore, the sanitary quality of such a product has to be controlled strictly in a process of manufacture and in a course of circulation for sale.

It is very important for this purpose that a microbial inspection be carried out rapidly and the result concerning microbial contamination be obtained as soon as possible.

Known methods for detecting microotganisms, however, require at least 24 hours incubation period for detection. As the conventional methods for detecting microorganisms, the Plate Count Method and the Most Probable Number Method are known (Official Methods of Analysis of the Association of Official Analytical Chemists, Official First Action, Eleventh Edition, page 843, 1970, U.S.A.), as follows: Plate Count Method (suitable for analyzing foods in which large number of microbes are expected.)

Sample (food) is homogenized and diluted with sterile water. Each decimal dilution of $10^{-1}$ to $10^{-4}$ of the homogenate is poured into a petri dish together with a nutrient agar medium. Then the dishes are incubated for 24 to 48 hours and the number of colonies grown on a plate is counted, on basis of which plate count per gram is determined. Most Probable Number (MPN) method (recommended for a use in a routine surveillance of foods in which a small number of microbes, especially coliform bacteria, may be expected.) The dilution of the homogenate is transferred into 3 to 5 fermentation tubes containing nutrient medium such as lactose bouillon medium and Brilliant Green Lactose Bie (BGL B) and the tubes are incubated for 24 to 48 hours. Then the number of tubes showing gas production is counted (positive presumptive test). Afterwards the confirmed test for coliform bacteria, on all positive presumptive tests, is conducted.

MPN is calculated using MPN Table on basis of the number of tubes showing gas production.

In either case, microorganisms in a nutrient medium have to be cultured till the growth of the microorganisms can be measured with the naked eye.

Accordingly, these common methods require at least 24 hours incubation period for detection and the product manufactured has to be stored till the result is obtained. Recently, a number of papers concerning rapid methods for detecting microorganisms have been published.

In these methods, changes of an impedance or, PH of culture medium, or the amount of consumed oxygen, or generated carbon dioxide gas, accompanied with the growth of microorganisms is measured and the number of microorganisms is determined based on the relationship between the resultant values and the number of microorganisms. However, these methods are accessible only for the inspection of a sample solution containing more than $10^5$/ml microorganisms.

Additionally, these values may be affected by coexisting materials, and these rapid methods are not satisfactory for practical use owing to their low accuracy and limited range of detection.

BRIEF SUMMARY OF THE INVENTION

According to the present invention, there is provided a rapid method for detecting microorganisms in a sample solution by means of a fluorescence analysis method using umbelliferone derivatives.

This new method comprises
(a) incubating an aqueous solution containing the sample solution and non-fluorescent umbelliferone derivative at a temperature within the range from 20° C. to 50° C. until fluorescent umbelliferone derivative is liberated in the solution by microorganisms contained in the sample solution,
(b) measuring the amount of liberated umbelliferone derivative, and
(c) determining a number of the microorganisms in the sample solution based on the amount of liberated umbelliferone derivative.

In this method, the non-fluorescent umbelliferone derivative are hydrolysed and a fluorescent umbelliferone derivatives such as umbelliferone or 4-methyl umbelliferone is liberated by the microorganisms contained in the sample solution, and the amount of the liberated umbelliferone derivative is approximately proportional to the number of the microorganisms. Therefore, the number of microorganisms can be determined on basis of this proportional relationship.

According to the method of the present invention, a microbial inspection of various kinds of materials such as food, beverage, water and toiletry articles, or a clinical inspection of microbial infection can be carried out within 1 to 12 hours.

DETAILED DESCRIPTION OF THE INVENTION

Figure 1:
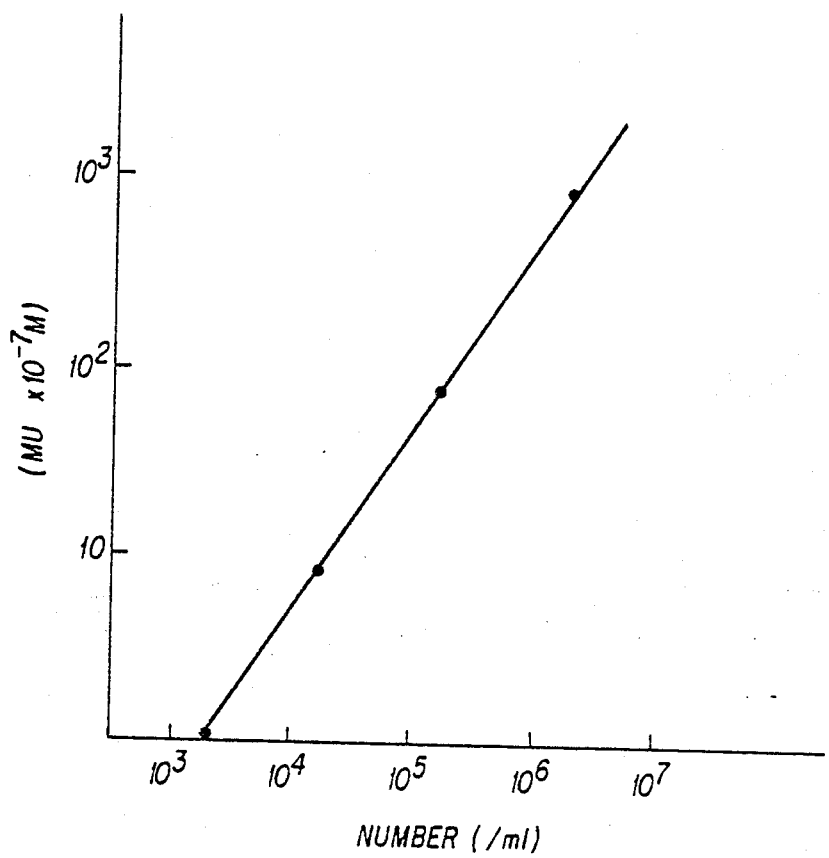

The non-fluorescent umbelliferone derivative employed according to the present invention is the compound of the following general formula

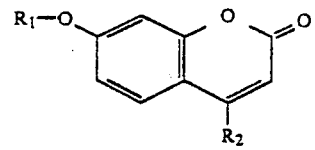

in which $R_1$ represents hexose residue, phosphate or acyl group, and $R_2$ represents hydrogen atom or lower alkyl group.

Examples of the umbelliferone derivative are 4-methylumbelliferyl phosphate (MUP), 4-methyl umbelliferyl pyrophosphate (MUPP), 4-methyl umbelliferyl α-D-galactoside (MUαGal), 4-methylumbelliferyl-β-D-galactoside (MUβGal), umbelliferyl-β-D-galactoside (UβGal), 4-methyl umbelliferyl alabinoside (MUAla), 4-methyl umbelliferyl acetate (MUAce), 4-methyl umbelliferyl acetoamido-β-D-glucoside (MUAG), and umbelliferyl glucoside.

Among these umbelliferone derivatives, MUP is more preferably used since MUP is hydrolysed by various kinds of microorganisms as shown in Table 1 in Example 1, and it is more preferable to use MUP together with MUPP, MUAG, MUGal, MUAce and/or MUALa, thereby a sensibility of detection is increased and time of detection can be reduced.

On the other hand, MUGal, and MUALa are suitable for detecting coliform bacteria selectively since they are hydrolysed only by coliform bacteria.

When the umbelliferone derivative is incubated with microorganisms it is hydrolysed and a fluorescent umbelliferone or 4-methyl umbelliferone is liberated. The incubated solution containing a fluorescent umbelliferone derivative fluoresces a light blue color of wave length 450 nm when exposed to an ultraviolet of wave length 360 nm, and the fluorescence can be sensed by a conventional fluorescence detector if more than $10^{-8}M$ umbelliferone derivative is liberated in the solution.

For sensing fluorescence, it is preferable to adjust the PH of the solution to alkali, more than 10.0, to increase the sensibility.

Microorganisms detected or determined according to the present invention are those which are aerobic bacteria and true fungi usually found in various kinds of food, water, and may grow on the standard nutrient agar medium.

Examples of aerobic bacteria are gram-negative bacteria such as bacteria belonging to the genus of Escherichia, Serratia, Pseudomonus, Klebsilla, Alcaligenes, and are grampositive bacteria belonging genus of Staphlococcus, Bacillus, Nocaldia, Brevibacterium, and Streptococcus.

The Examples of true fungi are those belonging genus of Saccharomyces, Candida, Aspergillus and Penicillium.

Coliform bacteria are those which are gram-negative, non-germ forming rods, and may decompose lactose and thereby produces gas. These contain bacteria belonging to the genus of Esherichia, Erwinia, Seratia, Proteus, Salmonella.

According to the method of the present invention, a number of microorganisms more than $10^4$/ml can be determined directly by contacting a sample solution with the umbelliferone derivative and measuring the amount of fluorescent umbelliferone derivative liberated.

Thus, $10^{-3}$ to $10^{-4}M$ umbelliferone derivative is added to a sample solution and the mixture solution is incubated for 10 minutes to 6 hours at a temperature ranging from 10° to 60° C. After an insoluble residue such as microbial cells is removed, fluorescence of the solution is sensed with a conventional fluorescence detector, and the amount of liberated umbelliferone is determined. The amount of liberated umbelliferone derivative is approximately proportional to the number of microorganisms as shown in Table 3 in Example 2 and in FIG. I in Example 4. Therefore, the number of microorganisms can be determined by obtaining in advance such a relationship. A number of microorganisms detectable according to this method, is about from $10^4$ to $10^7$/ml as shown in FIG. I.

In order to increase sensitivity, microbial cells in the sample solution may be ruptured by contacting them with an organic solvent such as toluene, chloroform, lytic enzyme, or by a physical method such as a sonic disintegration prior to the incubation or during the incubation. By the rupture, the enzyme capable of liberating fluorescent umbelliferone derivative usually contained in microbial cells is extracted, thereby the sensitivity of detection may be increased several times.

The sensitivity may be increased also by prolonging the period of the incubation, or concentrating the microbial cells so that a sample solution contains more than $10^4$/ml of microbial cells.

However, this direct method is insufficient for detecting a smaller number of microorganisms such as less than $10^3$/ml.

Smaller number of microorganisms less than $10^4$/ml can be determined by propagating microorganisms of a sample solution, prior to the determination, in a nutrient culture medium for 1 to 12 hours till they propagate more than $10^4$/ml in a culture medium.

As the number of microorganisms in the resultant culture broth is proportional to the cultivation time, the number of microorganisms can be determined according to the cultivation time and by measuring the number of microorganisms in the broth.

The number is also determined more accurately according to the procedure of the conventional MPN method previously described. That is, a sample solution or homogenate of sample is diluted with a sterile water to prepare decimal dilutions of $10^{-1}$ to $10^{-4}$ of the sample solution and each of the dilutions is put into three or five tubes containing a conventional nutrient culture medium. The tubes are then incubated for 1 to 12 hours to make microorganisms propagate in the tubes in the presence of the umbelliferone derivative.

The umbelliferone derivative can be added to the culture medium after the incubation when the incubation is carried out without addition of the umbelliferone derivative to the medium, and further 1 to 2 hours incubation is carried out.

Thereafter, the number of the tubes showing a fluorescence among the three or five tubes is counted in each dilution and the number of microbial cells is determined according to the MPN method previously mentioned. Nutrient media used in this method are conventional and commonly used in microbial detection. Example of these media are peptone media, Heart Infusion broth and Nutrient broth.

For detection of fungi, Zapek's Dox medium, Malt extract medium, Potato-Dextrose medium or Cornmeal medium are preferred.

In order to detect fungi selectively, antibiotics such as chloramphenicol or penicillin which inhibit bacterial growth are added to the nutrient medium.

In order to detect coliform bacteria, it is preferable to add a bile acid or desoxycholic acid which inhibits growth of microorganisms other than coliform bacteria to the nutrient culture medium. Since coliform bacterium has galactosidase specifically, it is preferable to add to the nutrient medium an inducer of galactosidase such as lactose isopropyl-β-D-thiogalactopyranoside (IPTG), propyl-β-D-thiolactopyranoside (PTG) and MUGal when MUGal is used as the umbelliferone derivative.

As described above, a rapid method for detecting or determining the number of microorganisms can be achieved by means of fluorescence analysis method and this new method will be practically useful for a microbial inspection of various kinds of food, beverage and water, and for clinical inspection of a microbial infection.

The invention will be illustrated by the following Examples.

EXAMPLE 1

A medium of pH 7.0 contain 0.5% peptone and $10^{-3}$M 4-methyl umbelliferone derivatives was prepared, and filtered through milliporfilter, and 3.0 ml portions of the medium were poured into 20 ml-test tubes aseptically. Each tube of the peptone medium was inoculated with 10 to 100 of microbial cells of known strains shown in Table 1 and incubated with shaking for 24 hours at 30° C. in case of bacteria or at 25° C. in case of fungi and yeast. The number of grown microorganisms in the culture medium varies but it is within the range of from $10^6$ to $10^9$ per ml.

TABLE 1

| List of Test Strains | |
|---|---|
| | ATCC Number |
| Coliform organisms | |
| *Escherichia coli* | 25922 |
| *Enterobacter cloacae* | 23355 |
| *Proteus vulgaris* | 13315 |
| *Serratia marcescens* | 8100 |
| *Salmonella typhimurium* | 14028 |
| *Klebsiella pneumoniae* | 13883 |
| Other Gram-negative bacteria | |
| *Pseudomonas aeruginosa* | 27853 |
| *Alcaligenes faecalis* | 25094 |
| Gram-positive bacteria | |
| *Staphylococcus aureus* | 25923 |
| *Staphylococcus epidernidis* | 12228 |
| *Bacillus cereus* | 14579 |
| *Nocardia asteroides* | 3308 |
| *Brevibacterium flavum* | 14067 |
| *Streptococcus faecalis* | 12984 |
| *Streptococcus pyogenes* | 19615 |
| Yeast | |
| *Saccharomyces cerevisiae* | (CBS 1171) |
| *Candida albicans* | 10231 |
| Fungi | |
| *Aspergillus niger* | 6275 |
| *Penicillium citrinum* | 9849 |
| *Acinetobacter calcoaceticus* | 23055 |

After the pH of each culture broth was adjusted to 11.0 with alkali, the medium was centrifuged to remove insoluble microbial cells and exposed to ultraviolet lights of wave length 360 nm. Then a fluorescence of wave length 450 nm was sensed with the fluorescence detector (Model 204S of Hitachi, Ltd., Tokyo) and the amount of the liberated 4-methyl umbelliferone (4-MU) was determined. The result obtained is shown in Table 2. As shown in Table 2, MUP is hydrolysed by all of the tested strains. On the other hand, MUβGal, MUαGal, and MUAla are hydrolysed selectively by bacteria belonging to coliform bacteria.

TABLE 2

| Tested strain (ATCC No.) | Activities of liberating 4-MU of test strains Amount of 4-MU liberated MU derivatives tested | | | | | | | |
|---|---|---|---|---|---|---|---|---|
| | MUP | MUGal | MUPP | MUAce | MUAG | MUαGal | MUβGal | MUALa |
| 25922 | +++ | + | ++ | + | ++ | +++ | +++ | +++ |
| 23355 | +++ | ++ | ++ | + | ++ | +++ | +++ | +++ |
| 13342 | +++ | − | ++ | + | + | − | − | − |
| 8100 | +++ | ++ | ++ | − | ++ | − | ++ | +++ |
| 14028 | +++ | + | − | ± | + | − | − | − |
| 13883 | +++ | − | ++ | + | ++ | − | − | ++ |
| 27853 | +++ | − | − | + | − | − | − | − |
| 25094 | + | − | − | + | − | − | − | − |
| 25923 | ++ | − | − | − | − | − | − | − |
| 12228 | ++ | − | − | − | − | − | − | − |
| 14579 | ++ | + | − | + | − | − | − | − |
| 3304 | + | + | − | + | ± | − | − | − |
| 12984 | + | + | − | − | + | − | − | − |
| 14067 | + | − | − | + | + | − | − | − |
| 19615 | ++ | − | − | − | − | − | − | − |
| CBS 1171 | ++ | − | + | − | − | − | − | − |
| 10231 | ++ | ++ | − | − | − | − | − | − |
| 6275 | + | ++ | − | ++ | − | − | − | − |
| 9849 | + | + | − | − | + | − | − | − |
| 23055 | ++ | + | − | − | − | − | − | − |

(−): 4-MU is not detected.
(+): Amount of 4-MU is more than $10^{-7}$M.
(++): Amount of 4-MU is more than $10^{-6}$M.
(+++): Amount of 4-MU is more than $10^{-5}$M.

EXAMPLE 2

Four sample solutions were collected from the Tama river water, the waste water of a food manufacturing factory, well water and sewerage, respectively, and each 10 ml portions of 16 sample solutions were poured into test tubes together with 1.0 ml phosphate buffer solution containing $1.1 \times 10^{-2}$M MUP. Each of the tubes was then allowed to stand at 37° C. for 2 hours. After insoluble residues were removed by centrifugation, the pH of the solution was adjusted to pH 10.5 and the amount of the liberated 4-MU was determined with a fluorescence detector.

On the other hand, the number of microorganisms of each sample solution was determined according to the common plate count method using a standard agar medium.

The relationship between the number of microorganisms and the amount of liberated 4-MU is shown in Table 3.

TABLE 3

| Relationship between number of microorganisms and amount of 4-MU liberated | | | |
|---|---|---|---|
| Number (per 10 ml) | 4-MU ($\times 10^{-7}$) | Number (per 10 ml) | 4-MU ($\times 10^{-7}$M) |
| $1.1 \times 10^2$ | 0 | $6.3 \times 10^6$ | 285 |
| $2.0 \times 10^3$ | 0 | $8.2 \times 10^6$ | 493 |
| $5.0 \times 10^3$ | 0 | $1.3 \times 10^7$ | 890 |
| $3.0 \times 10^4$ | 1.5 | $4.2 \times 10^7$ | 630 |
| $7.2 \times 10^4$ | 3.2 | $7.1 \times 10^7$ | 952 |

TABLE 3-continued

Relationship between number of microorganisms and amount of 4-MU liberated

| Number (per 10 ml) | 4-MU ($\times 10^{-7}$) | Number (per 10 ml) | 4-MU ($\times 10^{-7}$M) |
|---|---|---|---|
| $3.6 \times 10^5$ | 82 | $8.2 \times 10^8$ | 1300 |
| $4.2 \times 10^5$ | 93 | $1.9 \times 10^8$ | 930 |
| $5.1 \times 10^6$ | 305 | $2.1 \times 10^8$ | 1480 |

As shown in Table 3, the amount of liberated 4-MU is approximately proportional to the number of microorganisms measured by the common plate count method. Accordingly, the number of microorganisms in water can be measured by this new method extremely rapidly with almost the same accuracy as the common plate count method.

EXAMPLE 3

Ten grams of commercially available potato salad were weighed, to which 90 ml sterile water was added and mixed. The mixture was homogenized for 1.0 min. at 20,000 rpm and diluted with a sterile water to prepare decimal dilutions of $10^{-1}$, $10^{-2}$, and $10^{-3}$ of the homogenate. 1.0 ml portions of the dilution were transferred into 3 test tubes containing 9.0 ml of 0.05% peptone medium and they were incubated at 30° C. for 12 hours with shaking. After removing insoluble residues, fluorescence of the medium was sensed with a fluorescence detector in the same manner as described in Example 2. Then the number of the tubes showing fluorescence was counted, based on which MPN was determined using MPN Tables.

In parallel with this experiment, the number of microorganisms was determined according to the conventional MPN method. Thus, 1.0 ml of the dilution was transferred into 3 tubes containing 9.0 ml nutrient culture medium (containing yeast extract 0.25%, peptone 0.5% and glucose 0.1%, of PH 7.1). And the medium was incubated at 30° C. for 48 hours, then it was observed whether microorganism grows in the medium or not on basis of the tubidity of the medium and the number of the tubes showing the growth of microorganisms was determined, on basis of which MPN was determined using MPN Tables.

By the same way, the number of microorganisms of commercially available macaroni salad and spaghetti salad were determined. The results obtained are shown in Table 4.

TABLE 4

MPN of salads (per 10 grams)

| Kind of salad | Method of present invention (12 hours) | Conventional Method (48 hours) |
|---|---|---|
| Potato | $1.5 \times 10^5$ | $1.1 \times 10^5$ |
| Macaroni | $4.3 \times 10^3$ | $7.5 \times 10^3$ |
| Spaghetti | $7.5 \times 10^4$ | $9.3 \times 10^4$ |

MPN of the same potato salad was determined by the same manner as described above except for using the peptone medium containing $10^{-3}$M MUP. $10^{-3}$M MU-Gal, and $10^{-3}$M MUβGal, and the same MPN ($1.5 \times 10^5$) was obtained with 10 hours incubation.

EXAMPLE 4

*Escherichia coli* ATCC 25922 was cultured at 37° C. while shaking in Heart Infusion (HI) medium containing 0.05% sodium desoxychalate and $10^{-2}$M IPTG. After 8 hours, the medium was diluted with phosphate buffer solution containing $3 \times 10^{-4}$M of MUβGal so that $10^2$/ml microbial cells was contained in it. Then 5.0 ml dilutions were poured into test tubes with 20 μl toluene and the tubes were allowed to stand at 40° C. for an hour and an amount of liberated 4-MU was measured in the same manner as described in Example 2.

The results obtained are shown in FIG. I, in which the axis of abscissa shows the number of microorganisms determined according to the conventional plate count method, the axis of ordinate shows the amount of liberated 4-MU($\times 10^{-7}$M).

In FIG. I, there is indicated the linear relationship between the number of microorganisms and the amount of liberated 4-MU.

On the other hand, samples of urine was collected from 5 urethra-infected patients according to the conventional method and each of 4.5 ml portions of the urine were poured into test tubes together with 4.5 ml HI medium, which is the same medium as that used in the above experiment except that it had previously been concentrated two times, and the tubes were incubated at 37° C. for 8 hours with shaking. Then 20 μl toluene and 1.0 ml phosphate buffer solution containing $5 \times 10^{-4}$M of MUβGal was added to each the tubes and further 1.0 hour's incubation was carried out at 40° C.

Thereafter the amount of liberated 4-MU in the solution was sensed and the number of coliform bacteria was determined using the relationship indicated in FIG. I. The results obtained are shown in Table 5, in which the number of the coliform bacteria in the urine determined according to the conventional plate count method are shown as the control.

TABLE 5

Number of coliform bacteria in urine

| Urine sample | Method of the present invention (per 1 ml) | Plate count method (per 1 ml) |
|---|---|---|
| A | $4.6 \times 10^5$ | $4.8 \times 10^5$ |
| B | $2.0 \times 10^7$ | $1.8 \times 10^7$ |
| C | $1.0 \times 10^6$ | $2.0 \times 10^6$ |
| D | over | $4.8 \times 10^7$ |
| E | $3.5 \times 10^6$ | $3.0 \times 10^6$ |

EXAMPLE 5

*Escherichia coli* ATCC 10798 (K-12) was cultured at 37° C. for 20 hours with shaking in Bouillon medium containing 0.1% sodium desoxychalate.

The culture broth was stepwise diluted with a sterile water to prepare dilutions containing 10, $10^2$, $10^3$, $10^4$/ml microbial cells.

One ml portions of the dilutions were poured into test tubes together with 9.0 ml Bouillon medium containing $10^{-3}$M IPTG, and the tubes were incubated at 37° C. for 1.0 to 6.0 hours with shaking. Each 2.0 ml portion of the cultured medium was transferred into another test tube with 20 μl( toluene and 2.0 ml phosphate buffer solution containing $3 \times 10^{-3}$M of MUβGal. The tubes were then allowed to stand at 37° C. for 60 minutes, and the amount of liberated 4-MU was measured in the same manner as described in Example 2. The results obtained are shown in Table 6, in which the number of cells were determined according to the conventional plate count method.

TABLE 6

Relationship between number of microbial cells/10 ml and cultivation time

| Size of Inoculation (No/10 ml) | Cultivation time | | | | | | | | | |
|---|---|---|---|---|---|---|---|---|---|---|
| | 1 | | 2 | | 3 | | 4 | | 5 | |
| | Number | 4-MU | Number | 4-MU | Number | 4-MU | Number | 4-MU | Number | 4-MU |
| 0 | 0 | — | 0 | — | 0 | — | 0 | — | 0 | — |
| 1.0 | 4 | — | 3.2 | — | 260 | — | $2.1 \times 10^3$ | — | $1.6 \times 10^4$ | $1.3 \times 10^{-7}$ |
| 10 | 40 | — | 320 | — | $2.7 \times 10^3$ | — | $2.3 \times 10^4$ | $1.5 \times 10^{-7}$ | $1.6 \times 10^5$ | $1.5 \times 10^{-6}$ |
| $10^2$ | 400 | — | $3.2 \times 10^3$ | — | $2.6 \times 10^4$ | $2.1 \times 10^{-7}$ | $2.2 \times 10^5$ | $1.4 \times 10^{-6}$ | $1.6 \times 10^7$ | $1.4 \times 10^{-5}$ |
| $10^3$ | $4 \times 10^3$ | — | $3.2 \times 10^4$ | $2.5 \times 10^{-7}$ | $2.6 \times 10^5$ | $1.7 \times 10^{-6}$ | | | | |
| $10^4$ | $4 \times 10^4$ | $2.8 \times 10^{-7}$ | $3.2 \times 10^5$ | $1.8 \times 10^{-6}$ | | | | | | |

In Table 6, there is shown the relationship between the numbers of microbial cells and time of cultivation regarding each culture medium containing 10 to $10^4$ microbial cells.

Accordingly, a small number of microbial cells of E. coli may be determined based on this relationship.

EXAMPLE 6

Heart Infusion (HI) medium containing $10^{-3}$M IPTG, PTG or 1.0% lactose which is an inducer of β-galactosidase was prepared. 10 ml portions of the media were inoculated with 100 microbial cells of *Escherichia coli* ATCC 10798 (K-12) and incubated at 37° C. with shaking for 5 hours. The numbers of microbial cells in the resultant culture medium were all $1.6 \times 10^6$ per ml.

Two ml portions of the media were transferred into test tubes together with 2.0 ml phosphate buffer solution containing $3 \times 10^{-4}$M of MUβGal. And the tubes were allowed to stand at 40° C. for an hour. The amount of liberated 4-MU was then measured in the same manner as described in Example 2, and the results are shown in Table 7.

TABLE 7

Effect of addition of inducer

| Inducer | Amount of 4-MU (M) |
|---|---|
| none | $1.5 \times 10^{-6}$ |
| IPTG | $1.5 \times 10^{-5}$ |
| PTG | $1.5 \times 10^{-5}$ |
| lactose | $8.7 \times 10^{-6}$ |

When the microbial cells of the culture medium containing $10^{-3}$M IPTG thus obtained were ruptured by contacting them with 5 μl/ml ethylacetate at 37° C. for an hour or by exposing them to sonic waves (10KH, 10 min.), the amount of liberated 4-MU was increased about 10 times that of the control as shown in Table 8.

TABLE 8

Effect of rupture of microbial cells

| treatment | amount of 4-MU (M) |
|---|---|
| none (control) | $1.5 \times 10^{-5}$ |
| Ethyl acetate | $1.5 \times 10^{-4}$ |
| Sonic disintegration | $1.5 \times 10^{-4}$ |

EXAMPLE 7

Ten ml HI medium containing $10^{-3}$M IPTG, 0.1% sodium desoxycholate and $10^{-3}$M umbelliferyl-β-D-galactoside was poured into 5 test tubes and 0.01 ml portions of river water from the Tama river were added to 5 tubes. Five tubes were then incubated at 37° C. for 6 hours with shaking.

In the same manner, 0.1 ml, 1.0 ml and 10 ml portions of the river water were added to other 5 tubes respectively and they were also incubated at 37° C. for 6 hours.

After insoluble residues were removed by centrifugation, fluorescence of the solution was sensed and MPN was determined based on the number of the test tubes having a fluorescence using MPN Tables.

On the other hand, MPN of the river water was determined according to the conventional MPN method.

For comparison HI medium containing only 0.1% sodium desoxycholate was poured into 5 fermentation tubes, and the river water was added to 5 tubes. Then they were cultured at 37° C. for 48 hours and the number of the tubes showing gas production was measured according to the conventional method. Then, MPN was determined based on the numbers of tubes using MPN Tables. The result obtained are shown in Table 8.

TABLE 8

MPN of river water

| Sample size (ml) | Number of positive tubes | |
|---|---|---|
| | fluorescence 6 hours | gas production 48 hours |
| 10* | 5 | 5 |
| 1.0 | 3 | 3 |
| 0.1 | 0 | 0 |
| 0.01 | 0 | 0 |
| MPN/100 ml | 79 | 79 |

*double concentrated HI medium was used.

EXAMPLE 8

A hundred g commercially available croquette which was left alone overnight at room temperature was mixed with 100 ml phosphate buffer solution (pH 7.0, 0.1 M). The mixture was homogenized for 1.0 minutes at 20,000 rpm and was diluted with the same buffer solution to prepare decimal dilutions of $10^{-1}$, $10^{-2}$, and $10^{-3}$ of the homogenate.

One ml portions of each dilution were transferred into 5 test tubes together with 9.0 ml HI medium containing 0.1% sodium desoxycholate. Then each tube was incubated at 44.5° C. with shaking.

Two ml portion of the incubated medium, 20 μl toluene, and 2.0 ml phosphate buffer solution containing $3 \times 10^{-3}$M MUP were put into other tubes, which was then allowed to stand at 37° C. for an hour. After insoluble residues were removed, the number of the tubes showing fluorescence was examined. And the results obtained are shown in Table 9, in which the results obtained according to the conventional MPN method for detecting coliform bacteria are also shown.

TABLE 9

| MPN of coliform bacteria in croquette | | |
|---|---|---|
| | Number of positive tubes | |
| dilution | fluorescence (10 hours) | gas production (48 hours) |
| 1.0 | 5 | 5 |
| $10^{-1}$ | 2 | 2 |
| $10^{-2}$ | 0 | 0 |
| $10^{-3}$ | 0 | 0 |
| MPN/100 g | 49 | 49 |

EXAMPLE 9

Ten g soil from an orchard was mixed with 90 ml sterile water and homogenized for 1.0 minutes. Then it was diluted with sterile water to prepare decimal dilution of $10^{-1}$, and $10^{-2}$ of the homogenate, and 1.0 ml portions of each dilution were transferred into 3 tubes containing 5.0 ml YM medium consisting of 0.05% yeast extract, 0.05% malt extract, 100γ/ml chloramphenicol, $10^{-3}$M MUβGal and $10^{-3}$M MUP (pH 6.0). Then each of the tubes was incubated at 27° C. for 12 hours with shaking.

The number of the tubes showing fluorescence was examined in the same manner as described in Example 2, and MPN determined on the basis of the number using MPN Tables was 1500 per 10 g soil. In parallel with this experiment, the number of microorganisms was determined according to a conventional plate count method. Thereafter, 1.0 ml portion of the dilution of the homogenate were mixed with 9 ml YM medium consisting of 0.3% yeast extract, 0.3% malt extract, 0.5% peptone, 100γ/ml chloramphenicol and 1.5% agar with PH of 6.5. Then the mixture was poured into petri dish and incubated at 27° C. After 48 hours incubation, the number of colonies grown on the plate, which were mainly yeasts and fungi was counted and the number of microorganisms determined was 1300 per 10 g soil.

What is claimed is:

1. A method for rapidly determining a small number of microorganisms, less than $10^4$ per 1 milliliter, in a sample, which comprises:
   (A) forming a nutrient-containing solution consisting essentially of a nutrient medium capable of supporting propagation of the microorganisms and an aqueous solvent;
   (B) mixing said solution with a non-fluorescent umbelliferone derivative;
   (C) introducing said sample which contains microorganisms into said solution;
   (D) allowing said microorganisms to propagate in said solution consisting essentially of said nutrient-containing solution, umbelliferone derivative and sample for 1 to 12 hours;
   (E) measuring the amount of fluorescent umbelliferone derivative liberated by action of propagated microorganisms with a fluorescence detector; and
   (F) determining the number of microorganisms less than $10^4$ per 1 milliliter of said sample based on the amount of liberated fluorescent umbelliferone derivative.

2. A method for rapidly determining a small number of microorganisms, less than $10^4$ per 1 milliliter, in a sample, which comprises:
   (A) forming a nutrient-containing solution consisting essentially of a nutrient medium capable of supporting propagation of the microorganisms and an aqueous solvent;
   (B) introducing said sample which contains microorganisms into said solution;
   (C) allowing said microorganism to propagate in said solution for 1 to 12 hours;
   (D) mixing said solution with a non-fluorescent umbelliferone derivative to provide a mixture;
   (E) incubating said mixture consisting essentially of said nutrient-containing solution, said sample and said nonfluorescent umbelliferone derivative for from 1 to 2 hours;
   (F) measuring the amount of fluorescent umbelliferone derivative liberated by action of propagated microorganisms with a fluorescence detector; and
   (G) determining the number of microorganisms less than $10^4$ per 1 milliliter of said sample based on the amount of libertated fluorescent umbelliferone derivative.

3. The method as set forth in claim 2, wherein the cells of the propagated microorganism are ruptured prior to the mixing step.

4. The method as set forth in claims 1 or 2, wherein the non-fluorescent umbelliferone derivative is a compound of the formula

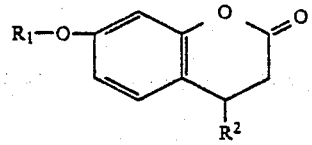

wherein
$R_1$ represents a hexose residue, phosphate pyrophosphate or acyl group, and
$R_2$ represents hydrogen or methyl group.

5. The method as set forth in claim 4, wherein $R_1$ is glucoside residue, arabinoside residue, galactoside residue, phosphate, pyrosphosphate or acetyl group and $R_2$ is a methyl group.

6. The method as set forth in claim 5, wherein $R_1$ is phosphate and $R_2$ is a methyl group.

7. The method as set forth in claims 1 or 2, wherein the microorganisms to be determined are coliform bacteria.

8. The method as set forth in claim 7, wherein 4-methyl umbelliferyl galactoside and/or 4-methyl umbelliferyl arabinoside is used as the umbelliferone derivative.

9. The method as set forth in claim 8, wherein an inducer of β-galactosidase is added to the sample.

10. The method as set forth in claims 1 or 2, wherein a bile acid or desoxycholate is added to the sample.

11. The method as set forth in claims 1 or 2, wherein the number of microorganisms is determined according to the conventional Most Probable Number method.

* * * * *